United States Patent
Yamamoto et al.

(10) Patent No.: US 9,431,775 B2
(45) Date of Patent: Aug. 30, 2016

(54) CONNECTOR WITH BUILT-IN ELECTRONIC CIRCUIT BOARD AND METHOD OF MANUFACTURING SAME

(71) Applicant: DENSO CORPORATION, Kariya, Aichi-pref. (JP)

(72) Inventors: Masahiro Yamamoto, Gamagori (JP); Hideyuki Kato, Nishio (JP)

(73) Assignee: DENSO CORPORATION, Kariya (JP)

( * ) Notice: Subject to any disclaimer, the term of this patent is extended or adjusted under 35 U.S.C. 154(b) by 34 days.

(21) Appl. No.: 14/465,447

(22) Filed: Aug. 21, 2014

(65) Prior Publication Data

US 2015/0056864 A1   Feb. 26, 2015

(30) Foreign Application Priority Data

Aug. 22, 2013   (JP) .................. 2013-172321

(51) Int. Cl.
| | |
|---|---|
| H01K 1/00 | (2006.01) |
| H01R 13/66 | (2006.01) |
| H01R 43/20 | (2006.01) |
| H01R 43/26 | (2006.01) |
| G01N 27/406 | (2006.01) |

(52) U.S. Cl.
CPC ...... *H01R 13/6683* (2013.01); *G01N 27/4062* (2013.01); *H01R 13/6658* (2013.01); *H01R 43/205* (2013.01); *H01R 43/26* (2013.01); *Y10T 29/49208* (2015.01)

(58) Field of Classification Search
CPC ............ H01R 13/6658; H01R 12/716; H01R 12/724; H01R 13/5213
USPC .................... 439/76.1, 620.22; 361/736, 752
See application file for complete search history.

(56) References Cited

U.S. PATENT DOCUMENTS

| | | | |
|---|---|---|---|
| 6,547,955 B1 | 4/2003 | Hada et al. | |
| 7,210,943 B1 * | 5/2007 | Chang ................ | H01R 13/6658 439/76.1 |

(Continued)

FOREIGN PATENT DOCUMENTS

| | | |
|---|---|---|
| JP | 60-158568 | 8/1985 |
| JP | 4-136753 | 5/1992 |

(Continued)

OTHER PUBLICATIONS

Office Action (2 pgs.) dated Jul. 21, 2015 issued in corresponding Japanese Office Action 2013-172321 with an at least partial English-language translation (2 pgs.).

*Primary Examiner* — Abdullah Riyami
*Assistant Examiner* — Thang Nguyen
(74) *Attorney, Agent, or Firm* — Nixon & Vanderhye P.C.

(57) ABSTRACT

A connector with built-in electronic circuit board includes an electronic circuit board for a sensor, the electronic circuit board including a first connection terminal, an inner case housing the electronic circuit board, and an outer case having a chamber housing the inner case. The connector further includes a second connection terminal extending from inside the chamber to outside the outer case, a third connection terminal disposed in the chamber, and a cable connected to the sensor at one end thereof at outside the outer case and connected to the third connection terminal at the other end thereof. The inner case is sealed by resin in a state of the first connection terminal being exposed. The first connection terminal is connected to the second and third connection terminals. The chamber is closed by a lid.

12 Claims, 4 Drawing Sheets

(56) References Cited

U.S. PATENT DOCUMENTS

| | | | | |
|---|---|---|---|---|
| 7,667,976 | B2* | 2/2010 | Sugimoto | H05K 1/182 174/260 |
| 7,722,362 | B2* | 5/2010 | Frake | B29C 43/18 439/76.1 |
| 8,197,284 | B2* | 6/2012 | Kim | H01R 13/6658 29/25.03 |
| 8,310,833 | B2* | 11/2012 | Sugimoto | H05K 3/284 174/520 |
| 8,469,718 | B2* | 6/2013 | Kobayashi | G01N 27/4062 439/55 |
| 2003/0155238 | A1 | 8/2003 | Hada et al. | |
| 2004/0087192 | A1* | 5/2004 | Ohta | H02G 3/088 439/76.1 |
| 2007/0161269 | A1* | 7/2007 | Sugimoto | B29C 45/14065 439/76.1 |
| 2008/0026610 | A1 | 1/2008 | Frake et al. | |
| 2009/0137135 | A1* | 5/2009 | Yamaguchi | H01R 13/521 439/76.1 |
| 2009/0163053 | A1* | 6/2009 | Yamaguchi | H01R 9/2466 439/76.1 |
| 2009/0177038 | A1* | 7/2009 | Yashiro | A61B 1/0051 600/132 |
| 2012/0184142 | A1* | 7/2012 | Furukawa | H01R 43/24 439/620.22 |
| 2014/0148019 | A1* | 5/2014 | Sasaki | H01R 13/516 439/65 |

FOREIGN PATENT DOCUMENTS

| | | |
|---|---|---|
| JP | 5-145085 | 6/1993 |
| JP | 6-260777 | 9/1994 |
| JP | 10-79398 | 3/1998 |
| JP | 10-209649 | 8/1998 |
| JP | 2000-171435 | 6/2000 |
| JP | 2004-342799 | 12/2004 |
| JP | 2010-530541 | 9/2010 |
| JP | 2012-069840 | 4/2012 |
| JP | 2013-137270 | 7/2013 |

* cited by examiner

CONNECTOR WITH BUILT-IN ELECTRONIC CIRCUIT BOARD AND METHOD OF MANUFACTURING SAME

This application claims priority to Japanese Patent Application No. 2013-172321 filed on Aug. 22, 2013, the entire contents of which are hereby incorporated by reference.

BACKGROUND OF THE INVENTION

1. Field of the Invention

The present invention relates to a connector with built-in electronic circuit board, which is suitable for a sensor that outputs a weak signal, such as a gas sensor.

2. Description of Related Art

Japanese Patent Application Laid-open No. 2000-171435 describes a connector incorporating a control circuit board of a sensor. Such a connector enables disposing the control circuit board of the sensor between the sensor and a control device. The control circuit board on which electronic parts are soldered is mounted on a connector case of the connector connected with a cable to be connected to the sensor, and sealed by a lid or the like.

When the sensor is a gas sensor that outputs a weak signal, such as an NOx sensor or a PM sensor, it is preferable to dispose the control circuit of the sensor in the vicinity of the sensor. However, since the temperature in the vicinity of an exhaust pipe on which the gas sensor is mounted is high (approximately 125 degrees C.), when the control circuit board is a resin board, there is a concern that the solder joint portions between the control circuit board and the electronic parts cannot withstand thermal stress.

Further, when the gas sensor is provided with a heater, since the control circuit for controlling the heater generates heat, a heat dissipation structure has to be provided in the gas sensor. Further, the gas sensor has to be resistant to external radio waves because it outputs a weak signal, and also has to be water and air proof because it is mounted under the floor of a vehicle body.

Hence, such a control circuit board must be resistant to high temperature, such as a ceramic board.

However, since the ceramic board is expensive, the manufacturing cost of such a gas sensor has been high.

SUMMARY

An exemplary embodiment provides a connector with built-in electronic circuit board including:

an electronic circuit board for a sensor, the electronic circuit board including electronic parts mounted thereon and provided with a first connection terminal;

an inner case having an opening at one side thereof through which the electronic circuit board can be inserted, the other sides of the inner case being closed;

an outer case having a chamber to which the inner case can be inserted;

a second connection terminal extending from inside the chamber to outside the outer case;

a third connection terminal disposed in the chamber; and a cable connected to the sensor at one end thereof at outside the outer case and connected to the third connection terminal at the other end thereof;

the electronic circuit board being housed in the inner case and sealed by resin in a state of the first connection terminal being exposed, the inner case being housed in the chamber of the outer case, the first connection terminal being connected to the second and third connection terminals, the chamber being closed by a lid.

The exemplary embodiment provides also a method of manufacturing the connector having the above described structure, the method including:

a first step of disposing the electronic circuit board in the inner case and sealing the electronic circuit board by resin in a state of the first connection terminal being exposed;

a second step of housing the inner case in the chamber of the outer case and connecting the first connection terminal to the second and third connection terminals; and a third step of closing the chamber by a lid.

Other advantages and features of the invention will become apparent from the following description including the drawings and claims.

PREFERRED EMBODIMENTS OF THE INVENTION

Figure 1:
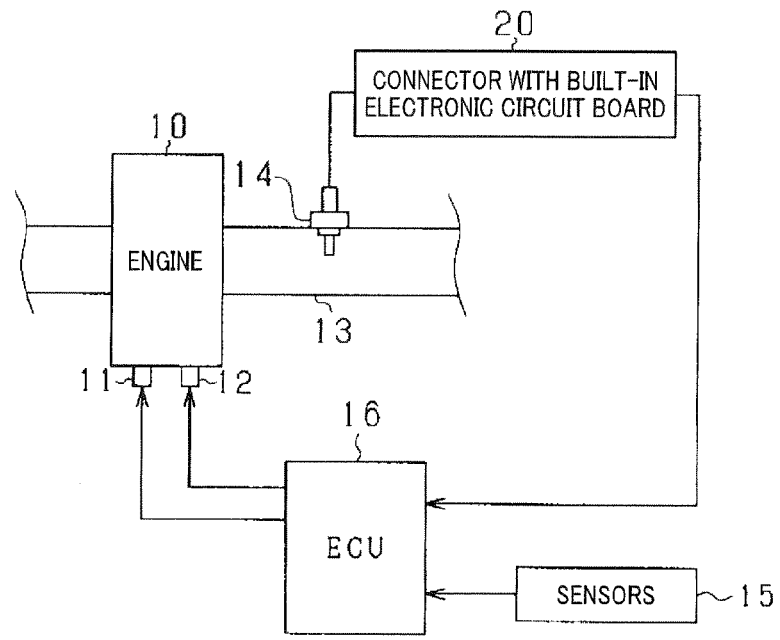
FIG. 1 is a diagram schematically showing a structure of a control system for controlling a vehicle engine, the control system including a gas sensor connected to a connector with built-in electronic circuit board according to a first embodiment of the invention.

In the below described embodiments, the same or equivalent parts, portions or components are indicated by the same reference numerals.

First Embodiment

The first embodiment is for a control system which performs various control operations on a vehicle engine based on the output of a gas sensor mounted on an exhaust pipe of the vehicle engine. The control system is constituted mainly of an ECU (electronic control unit) 16 which performs control of a fuel injection amount, ignition timing and so on. FIG. 1 is a diagram schematically showing the structure of the control system.

In FIG. 1, the reference numeral 10 denotes a gasoline engine including fuel injection valves 11 and ignition devices 12. The engine 10 is provided with an exhaust pipe 13 on which a gas sensor 14 is mounted. Various sensors 15 are mounted on the vehicle. The ECU 16 generates control signals based on output signals received from the gas sensor 14 and various sensors 15 and transmits them to the fuel injection valves 11 and the ignition devices 12.

The reference numeral 20 denotes a connector with built-in electronic circuit board. The connector 20 incorporates therein the electronic circuit board 30 for controlling the gas sensor 14. The gas sensor 14 is connected to the ECU 16 through the connector 20.

Figure 2A:
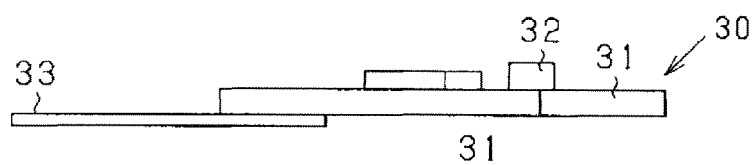
FIG. 2A is a side view of the electronic circuit board.
Figure 2B:
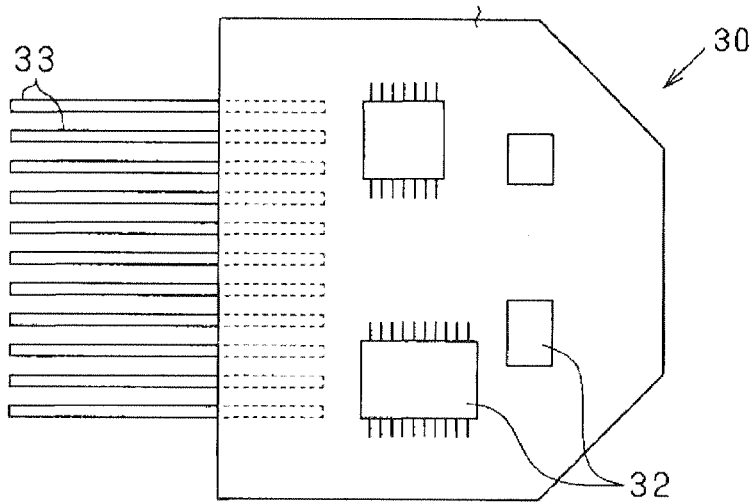
FIG. 2B is a top view of the electronic circuit board.

FIG. 2A is a side view of the electronic circuit board 30. FIG. 2B is a top view of the electronic circuit board 30. The electronic circuit board 30 includes a printed circuit board 31. The printed circuit board 31 is a glass epoxy board made by impregnating glass fiber fabric with epoxy resin. Electronic parts 32 such as ICs are mounted on the printed circuit board 31 by soldering. The printed circuit board 31 is fitted with a first connection terminal 33 by soldering at one end thereof.

Figure 3A:
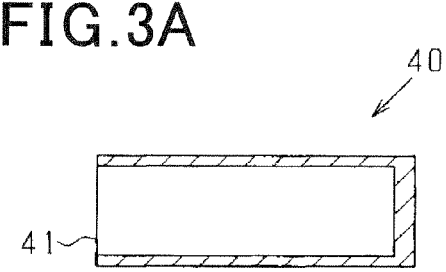
FIG. 3A is a longitudinal cross-sectional view of an inner case housing the electronic circuit board.
Figure 3B:
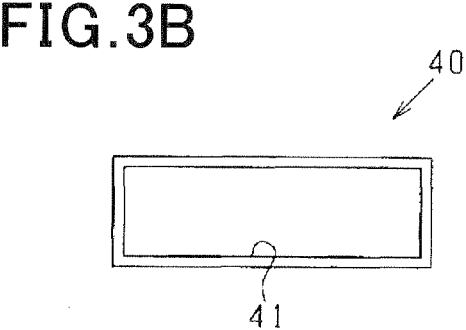
FIG. 3B is a front view of the inner case.
Figure 3C:
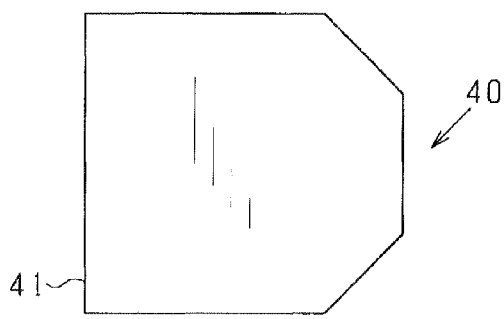
FIG. 3C is a top view of the inner case.

FIG. 3A is a longitudinal cross-sectional view of an inner case 40 for housing the electronic circuit board 30. FIG. 3B is a front view of the inner case 40. FIG. 3C is a top view of the inner case 40. The inner case 40 includes an opening 41 at one surface thereof. The electronic circuit board 30 can be inserted into the inner case 40 through the opening 41. The other sides of the inner case 40 are closed. The inner case 40 may have any shape as long as the first connection terminal 33 is exposed when the electronic circuit board 30 is housed in the inner case 40. That is, the inner case 40 has such a width that the electronic circuit board 30 can be accommodated and such a depth that the printed circuit board 31 is not exposed from the opening 41 and the first connection terminal 33 is exposed from the opening 41 when the electronic circuit board 30 is housed in the inner case 40. The height of the inner case 40 is such that the electronic circuit board 30 on which the electronic parts 32 are mounted can be housed therein. The material of the inner case 40 is preferably steel in view of the cost and electromagnetic shield effect. However, it may be aluminum or copper, or a shielding resin having electromagnetic shielding properties. When the connector 20 is used in an environment where the electromagnetic shield effect is not required, there is no such restriction for the material.

Figure 4A:
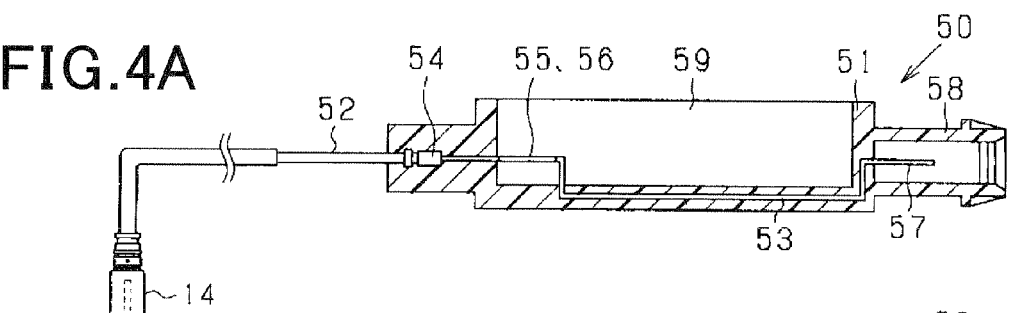
FIG. 4A is a longitudinal cross-sectional view of an outer case housing the inner case.
Figure 4B:
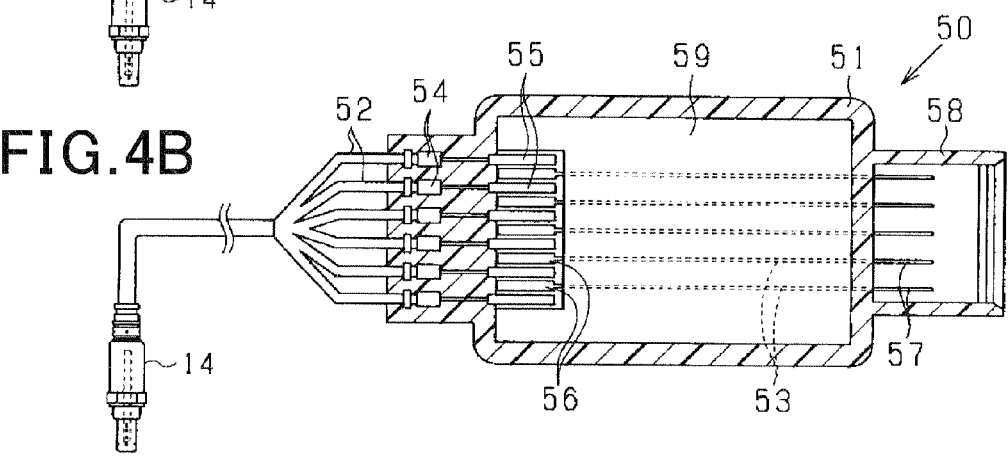
FIG. 4B is a lateral cross-sectional view of the outer case.

FIG. 4A is a longitudinal cross-sectional view of an outer case 50 for housing the inner case. FIG. 4B is a lateral cross-sectional view of the outer case 50. The outer case 50 includes a resin case member 51, a cable 52, a second connection terminal 53, a junction part 54 and a third connection terminal 55. The resin case member 51 includes a coupling part 58 for connection with the ECU 16 and a chamber 59. The resin case member 51 has a rectangular shape. The chamber 59 opens to the top side of the resin case member 51.

The cable 52 is connected to the gas sensor 14 at one end thereof and connected to the third connection terminal 55 through the junction part 54 at the other end thereof. The third connection terminal 55 is exposed to the chamber 59 of the outer case 50.

The second connection terminal 53 is formed with a first connection part 56 at one end thereof and formed with a second connection part 57 at the other end thereof. The first connection part 56 is exposed to the chamber 59. The second connection part 57 extends inside the coupling part 58.

The width and length of the chamber 59 are such that the inner case 40 housing the electronic circuit board 30 can be housed therein. The depth of the chamber 59 is such that the top side of the inner case 40 housed in the chamber 59 is below the top side of the resin case member 51. That is, the depth of the chamber 59 is such that a gap is present between a later-described lid 71 and the inner case 40 after the lid 71 is fitted to the resin case member 51.

The outer case 50 is fabricated by insert-molding where the cable 52, the third connection terminal 55 and the second connection terminal 53 are placed in a mold for the resin case member 51 after the cable 52 and the third connection terminal 55 are connected to each other, and then resin as the material of the resin case member 51 is poured into the mold. At this time, the junction part 54 between the cable 52 and the third connection terminal 55 is embedded in the resin of the resin case member 51. Since the resin case member 51 has to be heat-resistant, it is preferable that the resin case member 51 is made of polyphenylene sulfide resin (PPS), polybutylene terephthalate (PBT) or the like.

Next, a method of manufacturing the connector 20 is described.

Figure 5:
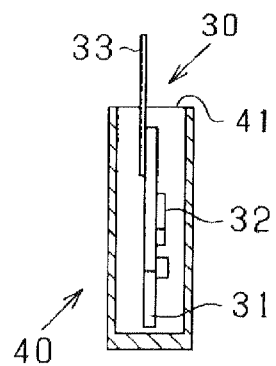
FIG. 5 is a diagram for explaining a step of housing the electronic circuit board in the inner case.

First, as shown in FIG. 5, the inner case 40 is placed with the opening 41 up, and then the electronic circuit board 30 is housed in the inner case 40. At this time, the first connection terminal 33 of the electronic circuit board 30 is exposed from the opening 41 of the inner case 40, but the printed circuit board 31 of the electronic circuit board 30 is not exposed from the opening 41 of the inner case 40.

Figure 6:
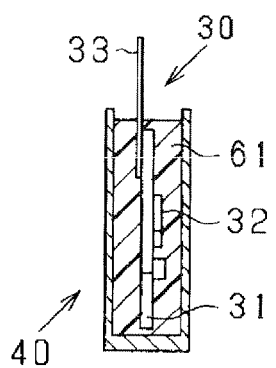
FIG. 6 is a diagram for explaining a step of sealing the electronic circuit board housed in the inner case using resin.

Subsequently, as shown in FIG. 6, the epoxy resin 61 is poured into the inner case 40 housing the electronic circuit board 30, and heated to be hardened. Preferably, the epoxy resin 61 is low-stress epoxy resin having a thermal expansion coefficient close to that of the printed circuit board 31, so that the thermal stress due to the difference between the thermal expansion coefficients of the printed circuit board 31 and the epoxy resin 61 can be made small.

After completion of the above steps, since the electronic circuit board 30 is protected by the epoxy resin 61 except the first connection terminal 33, it is easy to carry out an electrical test on the electronic circuit board 30. Accordingly, it is preferable to carry out the electrical test on the electronic circuit board 30 after completion of the above steps.

Figure 7:
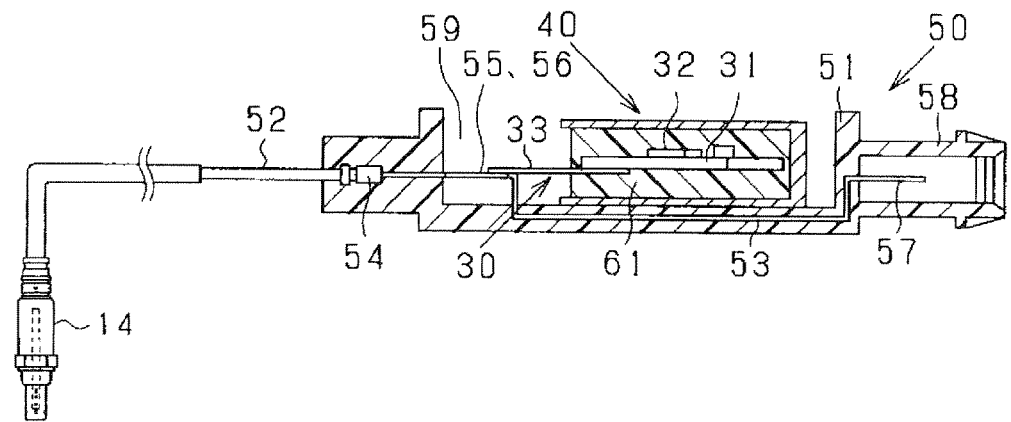
FIG. 7 is a diagram for explaining a step of housing the inner case in a chamber provided in the outer case.

Next, as shown in FIG. 7, the inner case 40 is housed in the chamber 59 of the outer case 50, and then the first connection terminal 33 of the electronic circuit board 30 is connected to the third connection terminal 55 and the first connection part 56 of the second connection terminal 53 by laser welding, resistance welding or the like.

Figure 8:
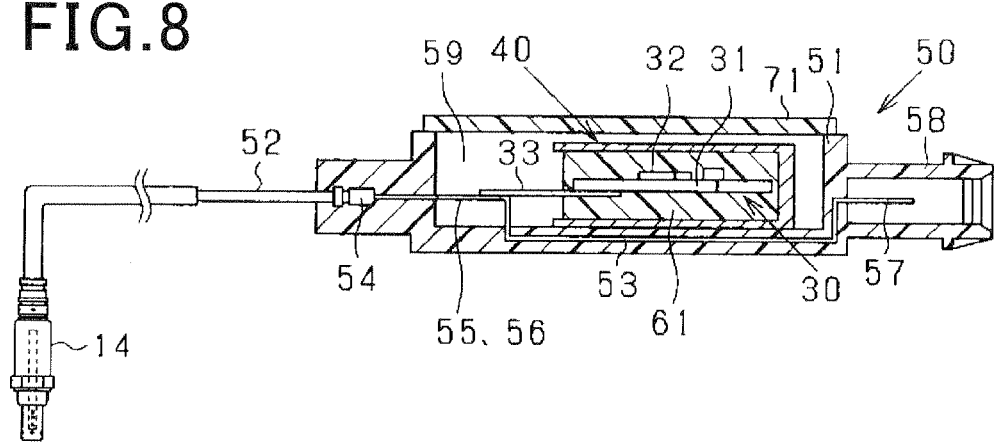
FIG. 8 is a longitudinal cross-sectional view of the finished connector with built-in electronic circuit board.

Finally, as shown in FIG. 8, the chamber 59 of the outer case 50 is closed by the lid 71. The lid 71 is fitted by laser welding or the like. As a result, the chamber 59 becomes sealed.

The connector 20 having the structure described above provides the following advantages.

Generally, the electronic parts 32 mounted on the electronic circuit board 30 generate heat. The heat generated by the electronic parts 32 is transmitted to the inner case 40 through the epoxy resin 61 sealing the electronic circuit board 30 and dissipated from the inner case 40. Accordingly, the connector 20 is not required to include a specific heat dissipation structure. Incidentally, since the thermal conductivity of resin is generally higher than that of the air, the heat transmission from the electronic circuit board 30 to the inner case 40 is greater when the electronic circuit board 30 is sealed by the epoxy resin 61 than when it is not sealed by the epoxy resin 61.

Since the electronic circuit board 30 is sealed by the epoxy resin 61, the heat stress applied to the solder joint portions of the electronic parts 32 can be reduced. More specifically, since the thermal expansion coefficients of the printed circuit board 31 of the electronic circuit board 30 and the epoxy resin 61 are close to each other, the thermal stress occurring due to contact between the substances having the different thermal expansion coefficients and applied to the solder joint portions of the electronic parts 32 can be suppressed.

When the inner case 40 is made of metal or shielding resin, electromagnetic shield effect against external noise can be obtained to increase the signal reliability of the electronic circuit board 30.

Since the junction part 54 between the cable 52 and the third connection terminal 55 is embedded in the resin case member 51, the stress applied to the junction part 54 can be reduced to thereby suppress a leak current due to possible damage of the junction part 54.

Since the connecting portion between the first connection terminal 33 and the second and third connection terminals 53 and 55 is exposed from the inner case 40, the heat resistance of the connecting portion is lower than that of the inside of the inner case 40 filled with the epoxy resin 61. Accordingly, to increase the heat resistance reliability, laser welding or resistance welding is employed to avoid use of solder which is low in heat resistance.

Since the chamber 59 is hermetically closed by the lid 71 and accordingly moisture can be prevented from entering the chamber 59, it is possible to prevent the first connection terminal 33, the second connection terminal 53 and the third connection terminal 55 from being corroded.

The inner case 40 includes the opening 41 at one side, the other sides being closed. Accordingly, the epoxy resin 61 can be poured into the inner case 40 through the opening 41, and can be prevented from leaking outside the inner case 40. Hence, the electronic circuit board 30 can be sealed easily by the epoxy resin 61.

Figure 9:
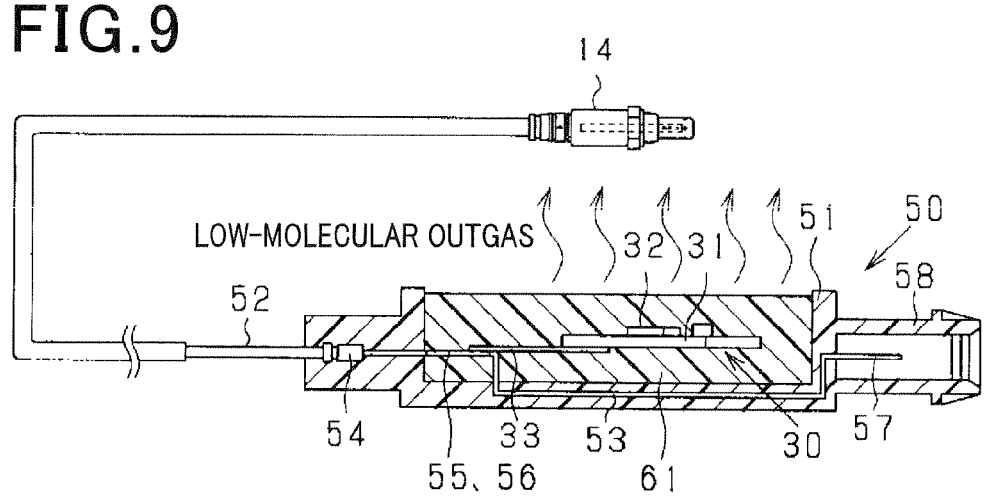
FIG. 9 is a longitudinal cross-sectional view of a comparative example of the connector with built-in electronic circuit board.
Figure 10:
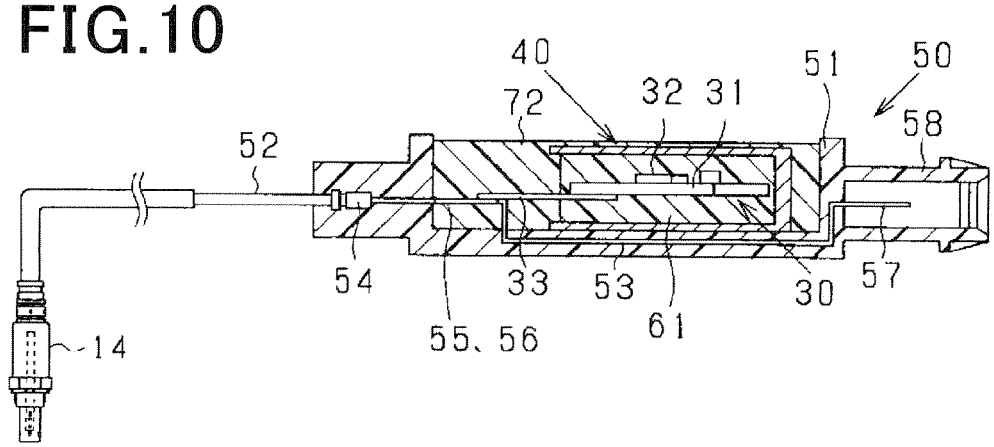
FIG. 10 is a longitudinal cross-sectional view of a connector with built-in electronic circuit board according to a second embodiment of the invention.

FIG. 9 shows the longitudinal cross-sectional view of a comparative example of the connector 20, in which the inner case 40 is not included, and the electronic circuit board 30 is housed in the chamber 59 of the outer case 50 and sealed by the epoxy resin 61.

When the electronic circuit board 30 is housed directly in the chamber 59 of the outer case 50, and the epoxy resin 61 is poured into the chamber 59, since the resin case member 51 of the outer case 50 is insert-molded with the cable 52 connected to the gas sensor 14, low-molecular outgas generated when the epoxy resin 61 is hardened enters inside the gas sensor 14. As a result, there may occur a characteristic deviation or an age deterioration of the sensor element of the gas sensor 14 due to the low-molecular outgas.

Further, since the stress applied to the electronic circuit board 30 includes also the stress applied to the outer case 50, the thermal stress in this comparative example is larger than that in the first embodiment. Accordingly, since the piezoresistive effect in the electronic parts 32 is large, there is a concern that the resistances of the electronic parts 32 may deviate from their design values.

Further, when a large shock is applied to the outer case 50, since it is directly transmitted to the electronic circuit board 30, the electronic circuit board 30 may be damaged, or a separation may occur in the joint surface between the resin case member 51 and the epoxy resin 61, or cracks may occur in the epoxy resin 61. Accordingly, there is a concern that moisture may enter the electronic circuit board 30 through the separation or cracks and cause the electronic circuit board 30 to malfunction.

By manufacturing the connector 20 in accordance with the procedure described above, since the epoxy resin 61 can be thermally hardened before assembling the inner case 40 to the outer case 50, the low-molecular outgas generated when the epoxy resin 61 is thermally hardened does not affect the element.

The connector 20 manufactured in accordance with the procedure described above has the structure in which a gap is provided between the inner case 40 and the lid 71, a shock applied to the lid 71 is hardly transmitted to the electronic circuit board 30. In addition, since the lid 71 is fitted to the resin case member 51 by laser welding or the like, even if a shock is applied to the electronic circuit board 30, the risk of the electronic circuit board 30 being damaged is small compared to the comparative example.

Second Embodiment

Next, a second embodiment of the invention is described. The second embodiment differs from the first embodiment in that instead of closing the chamber 59 of the outer case 50 using the lid 71, thermoplastic resin 72 is poured into the chamber 59 to seal the chamber 59.

The connector with built-in electronic circuit board according to this embodiment is manufactured in accordance with the same procedure as the first embodiment until the first connection terminal 33 is connected to the second and third connection terminals 53 and 55 after the inner case 40 is housed in the outer case 50.

In this embodiment, after the inner case 40 is disposed in the outer case 50, and the first connection terminal 33 is connected to the second and third connection terminals 53 and 55, the thermoplastic resin 72 is poured into the chamber 59 of the outer case 50. Preferably, the thermoplastic resin 72 is polyamide or polyester hot-melt resin having a heat resistant property.

The connector according to the second embodiment manufactured in accordance with the above procedure provides the following advantages in addition to the advantage provided by the first embodiment.

Sealing of the chamber 59 of the outer case 50 is made only by pouring the thermoplastic resin 72 in the chamber 59, and accordingly the manufacturing efficiency is high compared to the first embodiment in which the lid 71 is used to close the chamber 59.

The thermoplastic resin 72 has a shock absorbing property. Accordingly, sealing the chamber 59 using the thermoplastic resin 72 makes it possible to reduce transmission of a shock applied to the outer case 50 to the electronic circuit board 30.

The thermoplastic resin 72 generates less outgas than thermosetting epoxy resin. Accordingly, if the thermoplastic resin 72 is poured in a state of the connector being connected with the gas sensor 14, the influence exerted on the sensor element of the gas sensor 14 can be made small.

The above explained preferred embodiments are exemplary of the invention of the present application which is described solely by the claims appended below. It should be understood that modifications of the preferred embodiments may be made as would occur to one of skill in the art.

What is claimed is:

1. A connector with built-in electronic circuit board comprising:
   an electronic circuit board for a sensor, the electronic circuit board including electronic parts mounted thereon and provided with a first connection terminal;
   an inner case having an opening at one side thereof through which the electronic circuit board can be inserted, the other sides of the inner case being closed;
   an outer case having a chamber to which the inner case can be inserted;

a second connection terminal extending from inside the chamber to outside the outer case;

a third connection terminal disposed in the chamber; and a cable connected to the sensor at one end thereof at outside the outer case and connected to the third connection terminal at the other end thereof;

the electronic circuit board being housed in the inner case and sealed by resin in a state of the first connection terminal being exposed, the inner case being housed in the chamber of the outer case, the first connection terminal being connected to the second and third connection terminals, the chamber being closed by a lid; and the first connection terminal being connected to the second and third connection terminal outside the inner case and inside the chamber.

2. The connector according to claim 1, wherein the outer case is made of resin, and integrally molded with the cable and the second and third connection terminals by insert-molding.

3. The connector according to claim 1, wherein the electronic circuit board is made of epoxy resin, and the resin sealing the electronic circuit board is made of epoxy resin.

4. The connector according to claim 1, wherein the first connection terminal is connected to the second and third connection terminals by welding.

5. A connector with built-in electronic circuit board comprising:

an electronic circuit board for a sensor, the electronic circuit board including electronic parts mounted thereon and provided with a first connection terminal;

an inner case having an opening at one side thereof through which the electronic circuit board can be inserted, the other sides of the inner case being closed;

an outer case having a chamber to which the inner case can be inserted;

a second connection terminal extending from inside the chamber to outside the outer case;

a third connection terminal disposed in the chamber; and a cable connected to the sensor at one end thereof at outside the outer case and connected to the third connection terminal at the other end thereof;

the electronic circuit board being housed in the inner case and sealed by resin in a state of the first connection terminal being exposed, the inner case being housed in the chamber of the outer case, the first connection terminal being connected to the second and third connection terminals, the chamber being sealed by thermoplastic resin, and the first connection terminal being connected to the second and third connection terminal outside the inner case and inside the chamber.

6. The connector according to claim 5, wherein the outer case is made of resin, and integrally molded with the cable and the second and third connection terminals by insert-molding.

7. The connector according to claim 5, wherein the electronic circuit board is made of epoxy resin, and the resin sealing the electronic circuit board is made of epoxy resin.

8. The connector according to claim 5, wherein the first connection terminal is connected to the second and third connection terminals by welding.

9. A method of manufacturing a connector with built-in electronic circuit board, the connector including:

an electronic circuit board for a sensor, the electronic circuit board including electronic parts mounted thereon and provided with a first connection terminal;

an inner case having an opening at one side thereof through which the electronic circuit board can be inserted, the other sides of the inner case being closed;

an outer case having a chamber to which the inner case can be inserted;

a second connection terminal extending from inside the chamber to outside the outer case;

a third connection terminal disposed in the chamber; and a cable connected to the sensor at one end thereof at outside the outer case and connected to the third connection terminal at the other end thereof;

the electronic circuit board being housed in the inner case and sealed by resin in a state of the first connection terminal being exposed, the inner case being housed in the chamber of the outer case, the first connection terminal being connected to the second and third connection terminals, the chamber being closed by a lid, the method comprising:

a first step of housing the electronic circuit board in the inner case and sealing the electronic circuit board by resin in a state of the first connection terminal being exposed;

a second step of housing the inner case in the chamber of the outer case and connecting the first connection terminal to the second and third connection terminals; and a third step of closing the chamber by a lid, wherein the first connection terminal is connected to the second and third connection terminals outside the inner case and inside the chamber.

10. A method according to claim 9, further comprising a step performed, before the second step, of insert-molding the outer case by pouring resin in the chamber in a state where the cable connected to the third connection terminal and the second connection terminal are placed in the chamber.

11. A method of manufacturing a connector with built-in electronic circuit board, the connector including:

an electronic circuit board for a sensor, the electronic circuit board including electronic parts mounted thereon and provided with a first connection terminal;

an inner case having an opening at one side thereof through which the electronic circuit board can be inserted, the other sides of the inner case being closed;

an outer case having a chamber to which the inner case can be inserted;

a second connection terminal extending from inside the chamber to outside the outer case;

a third connection terminal disposed in the chamber; and a cable connected to the sensor at one end thereof at outside the outer case and connected to the third connection terminal at the other end thereof;

the electronic circuit board being housed in the inner case and sealed by resin in a state of the first connection terminal being exposed, the inner case being housed in the chamber of the outer case, the first connection terminal being connected to the second and third connection terminals, the chamber being sealed by thermoplastic resin, the method comprising:

a first step of housing the electronic circuit board in the inner case and sealing the electronic circuit board by resin in a state of the first connection terminal being exposed;

a second step of housing the inner case in the chamber of the outer case and connecting the first connection terminal to the second and third connection terminals; and a third step of sealing the chamber by pouring thermoplastic resin into the chamber, wherein the first connection terminal is connected to the second and third connection terminals outside the inner case and inside the chamber.

12. A method according to claim 11, further comprising a step performed, before the second step, of insert-molding the outer case by pouring resin in the chamber in a state where the cable connected to the third connection terminal and the second connection terminal are placed in the chamber.

\* \* \* \* \*